United States Patent [19]
Reintjes et al.

[11] Patent Number: 6,049,381
[45] Date of Patent: *Apr. 11, 2000

[54] REAL TIME SUSPENDED PARTICLE MONITOR

[75] Inventors: John F. Reintjes, Alexandria, Va.;
Michael D. Duncan, Cheverly, Md.;
Rita Mahon, Silver Spring, Md.;
Lawrence L. Tankersley, Annapolis, Md.; Paul L. Howard, West Chester, Pa.; Martin Chamberlain; Thomas McKenna, both of Arlington, Va.

[73] Assignee: The United States of America as represented by the Secretary of the Navy, Washington, D.C.

[*] Notice: This patent is subject to a terminal disclaimer.

[21] Appl. No.: 08/143,370

[22] Filed: Oct. 29, 1993

[51] Int. Cl.⁷ .................................................. G01N 21/05
[52] U.S. Cl. ............................................................ 356/335
[58] Field of Search ................................... 356/335–343; 250/574, 222.2, 39, 73

[56] References Cited

U.S. PATENT DOCUMENTS

| | | | |
|---|---|---|---|
| 3,641,320 | 2/1972 | Stockham et al. | 356/335 |
| 4,288,162 | 9/1981 | Sakamoto et al. | 356/335 |
| 4,329,052 | 5/1982 | Colombo et al. | 356/335 |
| 4,393,466 | 7/1983 | Deindoerfer et al. | 356/335 |
| 4,804,267 | 2/1989 | Greenfield | 356/335 |
| 4,805,225 | 2/1989 | Clark | 382/15 |
| 4,981,362 | 1/1991 | deJong et al. | 356/436 |
| 4,999,513 | 3/1991 | Ito et al. | 250/575 |
| 5,011,285 | 4/1991 | Jorgensen et al. | 356/335 |
| 5,089,714 | 2/1992 | Ludlow et al. | 250/574 |
| 5,140,168 | 8/1992 | King | 250/575 |
| 5,141,324 | 8/1992 | Strand et al. | 356/441 |
| 5,150,228 | 9/1992 | Liu et al. | 359/7 |
| 5,150,229 | 9/1992 | Takesue et al. | 359/7 |
| 5,191,388 | 3/1993 | Kilham | 356/335 |

FOREIGN PATENT DOCUMENTS

| | | | |
|---|---|---|---|
| 0507746 | 10/1992 | European Pat. Off. | 356/335 |
| 0107201 | 6/1984 | Japan | 356/335 |
| 5045274 | 2/1993 | Japan | 356/335 |
| 1643995 | 4/1991 | Russian Federation | 356/335 |

OTHER PUBLICATIONS

Rajbenbach et al., "Compact Photorefractive Correlator for Robotic Applications", Applied Optics, vol. 31, No. 26, Sep. 10, 1992, pp. 5666–5674.

Liu et al., "Real–Time VanderLugt Optical Correlator the Uses Photorefractive GaAs", Applied Optics, vol. 31, No. 26, Sep. 10, 1992, pp. 5675–5680.

Casasent, "An Optical Correlator Feature Extractor Neural Net System", Optical Engineering, vol. 31, No. 5, May 1992, pp. 971–978.

Nicholson et al., "Optimization of an Updatable Optical Image Correlator", Optical Engineering, vol. 26, No. 5, May 1987, pp. 445–452.

Intel News Release, Intel and Nestor Deliver Second–Generation Neural Network Chip to DARPA, Feb. 12, 1993.

Intel/Nestor, Preliminary Information Ni1000 Recognition Accelerator, Apr. 1993.

Primary Examiner—Hoa Q. Pham
Attorney, Agent, or Firm—Thomas E. McDonnell; Edward Miles; William F. Eipert

[57] ABSTRACT

A method and apparatus for real-time monitoring of particulates in a fluid. The fluid is illuminated, and an image formed of the interior of the fluid. The image is then detected, and processed to determine the size, shape, etc. of particulates within the fluid.

34 Claims, 3 Drawing Sheets

REAL TIME SUSPENDED PARTICLE MONITOR

BACKGROUND OF THE INVENTION

1. Field of the Invention

This invention relates to a fluid monitoring apparatus for detecting the presence of and determining the characteristics of particulate matter suspended in a fluid. More specifically, this invention relates to a device for the real time identification of the size and shape of a particle within a fluid by forming an optical image of the fluid and analyzing the image.

2. Description of the Related Art

Determination of the quantity, characteristics, and types of particulate matter in fluids is important for many applications such as monitoring fluids in engines and rotating machinery, industrial quality control, food processing, medical analysis, and observing environmental controls. Current devices for monitoring particulate matter in fluids involve various mechanical, electrical, or optical means.

Purely mechanical means involve collecting particulate matter in suitable traps such as filters, screens, or magnetic plugs. Analysis of the particles is done by removing the traps and examining the collected matter. These devices do not provide for real time monitoring. Electrical based particle monitoring devices are based upon induced currents. By sensing or measuring the change in an electric current, the concentration of electrically conducting or nonconducting particles can be determined. However, this technique is not able to identify the size or shape of the particles. In conventional electrical-mechanical devices, such as electric chip detectors in engines, only electrically conducting particles are detected and the detectors provide no identification on the size or shape of the particles.

Optical devices have been used to determine the concentration, number, or size of particles. However, these devices are limited in their ability to identify the shape of particles. They identify the shape of particles by differentiation based on the degree of sphericity (or asymmetry) of the particles. Such devices illuminate a fluid sample and measure the intensity of the light scattered and/or transmitted at various detectors surrounding the sample. By comparing the intensity measured at the various detectors, a degree of sphericity or an asymmetry factor for the particle is determined. The particles are grouped by this degree of asphericity rather than identified or classified by the shape of the particle.

Similarly, the size of the particles is obtained by comparing the average intensity with a reference intensity or with the difference in intensity for a number of particles with a similar asphericity over time. This method yields information on the size of particles but does not provide real time size and shape identification.

Additionally, optical devices are subject to operating requirements that limit the number and type of applications for which they can be used. One such requirement is that the particles be passed one at a time or that the fluid be passed in a small volume through a specific point because the light illuminating the particles is directed to that specific point. Additionally, in monitors that simply measure the light scattered from a single particle, the determination of symmetry is based upon the distribution of light scattered from a single particle. In such monitors, the symmetry of a particle cannot be accurately determined if two or more particles are illuminated at the same time. These requirements limit the application to those in which either the position of the particle is known and controlled or only a small sample of the fluid volume is passed to a monitor.

Another limitation of optical devices results from their sensitivity to air bubbles within the fluid. Entrained air bubbles are only distinguished from other particles by the high degree of sphericity or symmetry of the air bubbles. To remedy this, some devices must be oriented so that the air bubbles float to the top or upper area of the chamber containing the sample and, therefore, are removed from the sensing area of the fluid. Other devices will account for air bubbles by ignoring all highly spherical particles in any analysis of particulate matter.

Real time human visual inspection of particles can be accomplished by providing a window through which an individual can view the fluid. However, this method is limited to fluids flowing at low rates of speed. While using a strobe lamp or pulsed light to create the visual effect of stopping the motion of the particles will allow visual inspections for fluids flowing at higher speeds, these increased speeds are far below those encountered in many applications, for example, the speed at which oil flows in aircraft engines. Additionally, visual inspection is limited to those applications in which the particles are of sufficient size to be viewed by an individual and to those applications in which the fluid is sufficiently transmissive to light of wavelengths which can be seen by humans.

An optical device which forms an image of the fluid would be advantageous because it would be able to combine the advantages of visual inspection with the advantages of optical devices. More specifically, by analyzing the image formed, an accurate and real time determination of the size and shape of particles within the fluid can be accomplished. Additionally, devices which are sensitive to a wide range of particle sizes and wavelengths of light can be made.

The need for a device and method which can identify the size and shape of particulate matter within a fluid becomes readily apparent when one considers the problem of monitoring for particulate debris in the oil of helicopter or other aircraft. Particulate debris in helicopter or other aircraft engines can cause engine failure and loss of life. As a helicopter engine ages, particles from the engine or gear box components (bearings and gears) tend to flake off into the engine's oil. The size, shape, and density of flakes, as well as other types of debris, in the oil are indicative of engine condition, and can indicate when engine failure is imminent. Currently, magnetic plugs are removed for visual inspection of debris to spot upcoming engine failure. However, this must be done frequently to ensure that no failures occur. This routine maintenance is costly, time consuming and often unnecessary. An oil debris monitoring system that provides real time information on the size and shape of particles within the oil will provide an early warning system for engine failure and can be used to record engine condition to identify when maintenance is needed. Thus, a system that can monitor size, shape, and density of particulate debris in engine oil in real time would be a welcome addition to the art.

SUMMARY OF THE INVENTION

It is an object of this invention to provide a system and method of using the system, for the real time monitoring of suspended particulate matter in a fluid that is capable of accurately identifying the size and shape of particles within a fluid.

Another object of the present invention is the provision of a system which will form and analyze an image of a fluid to accurately determine the size and shape of particles within the fluid.

A further object of the present invention is the provision of a system that accurately determines the size and shape of particles within a fluid, while distinguishing suspended particles from entrained air bubbles.

Another object of this invention is to provide a system which will accurately determine the size and shape of particles, even in the presence of a rapidly flowing fluid by using one or more pulsed light sources to allow imaging with a desired degree of spatial resolution.

Another object of this invention is to provide a system which can monitor a large volume of fluid without the need to know or control the position of particles in fluid.

Yet a further object of this invention is to provide a system which uses parallel processing, of which a neural network is an example, to analyze an image of a fluid volume to quickly and accurately identify and classify particle shapes within the fluid.

In accordance with these and other objects made apparent hereinafter, the invention concerns a method and apparatus for the real time monitoring of suspended particulates in a fluid in which the apparatus uses a pulsed light source and collimating optics to direct an optical beam into a fluid chamber through which is passing a fluid to be examined. An optical image of the fluid within the fluid chamber is formed responsive to the light, and the image detected. The detected image contains the necessary information to permit classification of particulates in the fluid according to shape, size, etc. Preferably, the image is analyzed in situ by dedicated hardware pre-programmed to the task.

BRIEF DESCRIPTION OF THE DRAWINGS

These and other objects, features and advantages of the invention will become better understood by reference to the following detailed description when considered in connection with the accompanying drawings wherein like reference numerals designate identical or corresponding parts throughout the several views and wherein.

DETAILED DESCRIPTION

Figure 1:
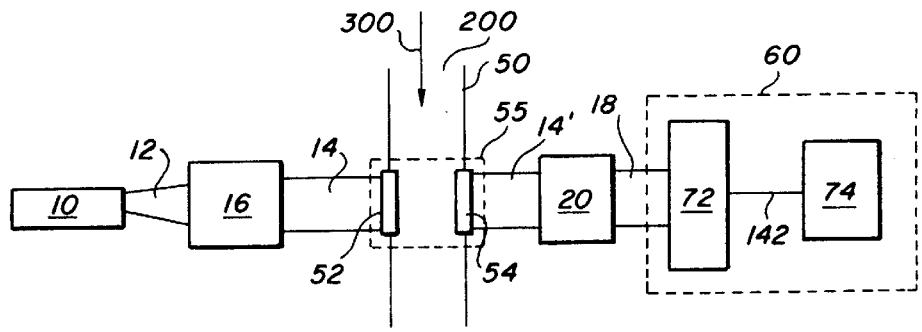
FIG. 1 is a schematic diagram illustrating a first embodiment of the present invention.

Referring now to FIG. 1, there is shown a first embodiment of the present invention. In FIG. 1, a fluid 200 to be monitored passes through fluid chamber 55. Fluid 200, either a liquid or a gas, flows in the direction from top to bottom of the sheet in FIG. 1, as indicated by reference arrow 300. Source 10 emits optical beam 12 into collimating optics 16. Optical beam 12 from source 10 can be either coherent or noncoherent, depending on the operation and application of the embodiment. Additionally, source 10 can emit beam 12 directly into collimating optics 16 (as shown in FIG. 1) or source 10 can be located some distance away with optical beam 12 directed to collimating optics 16 by conventional means, such as fiber optic cable. Collimating optics 16 produce a collimated beam 14 which illuminates fluid chamber 55. Collimated beam 14 preferably has an area such that the entire length, in the direction of the flow of the fluid, of fluid chamber 55 and the entire width, in the direction orthogonal to the sheet in FIG. 1, of fluid chamber 55 is illuminated. The collimation can be accomplished by any of several conventional means including, but not limited to, a lens, a mirror, or a lens and mirror combination. The collimating optics can also include optics for folding the beam to allow the source to be located physically adjacent to the fluid column 50.

Collimated beam 14, propagating in a direction from source 10 toward detector 72, enters fluid chamber 55 such that beam 14 is transverse to, and preferably orthogonal to, the flow of fluid 200. Fluid chamber 55 has a light transmitting portion 52 allowing collimated beam 14 to enter the fluid chamber and a second light transmitting portion 54 allowing optical beam 14' (the portion of collimated beam 14 transmitted through fluid 200) to exit fluid chamber 55. Light transmitting portions 52 and 54 bounding fluid chamber 55 should be of sufficient optical quality to allow imaging at the desired degree of spatial resolution.

Imaging system 20 uses optical beam 14' exiting fluid chamber 55 to form an image of fluid 200 within fluid chamber 55. The image formed by imaging system 20 is carried to optical detector 72 in optical beam 18. Optical detector 72 is an optically sensitive surface with two dimensional spatial resolution. The output of detector 72 is connected to shape classifier 74. Detector 72 converts the image formed on the optically sensitive surface into electronic data. This data is transferred to shape classifier 74 which analyzes the output data of detector 72 and identifies the size and shape of a particle in two dimensions based on characteristic patterns (straight lines, corners, curves, etc.). Together, optical detector 72 and shape classifier 74 form image processor 60. Both optical detector 72 and shape classifier 74 can be located some distance from fluid chamber 55 with the image carried to the image processor by conventional means, such as fiber optic cable. A complete description of the operation of image processor 60 is discussed below in reference to FIGS. 4A and 4B.

In operation, source 10 is pulsed so a "stop action" image of fluid 200 flowing within chamber 55 can be created. With each pulse, a new image of fluid 200 within fluid chamber 55 is created onto optical detector 72. Typically, in the time between pulses, the image is analyzed to determine the size and shape of the particles present in the fluid. The pulse duration and the pulse repetition rate are chosen with regard to the flow speed of fluid 200. The duration of the pulse should be short enough so that during the pulse the particles do not move by more than the desired spatial resolution. For example, oil flowing through an aircraft engine will flow through a fluid chamber at a maximum rate of 10 m/s. If the desired spatial resolution is 10 microns, the pulse duration should be 1 $\mu$s. The repetition rate is set so that, in the time between pulses, fluid 200 travels a distance equal to the length, in the direction of fluid flow, of the fluid imaged, thereby monitoring all the fluid passing through the chamber. For example, referring to the oil flowing in an aircraft engine, if the length of oil imaged is 1 cm, the time between pulses should be 1 ms (the time it takes the oil moving at 10 m/s to travel 1 cm). However, the repetition rate can be increased to allow the fluid to be imaged more than once as the fluid passes through the fluid chamber. Additionally, source 10 must emit optical beam 12 with a wavelength such that the beam can be transmitted through fluid 200 in sufficient quantity to be detectable yet at the same time be absorbed by the particulate matter within the fluid. For illuminating the oil used in aircraft engines, the wavelength of source 10 should be greater than 800-nm to allow a sufficient quantity of light to be transmitted through the oil, with a preferred wavelength being between 850 and 1000-nm. A single-mode diode laser with a wavelength of 850-nm can be used to illuminate the oil used in aircraft engines, although any source emitting light with the proper wavelength that is also capable of being pulsed at the proper repetition and duration rates can be used.

Shape classifier 74 can operate with any of a large number of known techniques to classify particulate shape, such as the techniques commonly used for character identification, adapted to specific particulate shapes of interest. Examples of such techniques are: template matching, e.g. two dimensional correlation between the image and a template image; or production of a spatial Fourier transforms of the image, and comparison with a template spectrum. One could also use neural net classifiers, with any commonly used classification techniques used with such neural nets, e.g. use of radial basis function networks, multilayer perceptions with back propagation, or adaptive resonance theory.

When forming the image of fluid 200 onto optical detector 72, the image plane will be at the entrance face of the optical detector, while the object plane will be set based upon the position of the particles. If the position of the particles in fluid 200 within fluid chamber 55 is known or controlled, such as with a narrow fluid chamber, that known position can be used as the object plane by the imaging system. Additionally, when the position of the particles is known or controlled such that the particles will always be in the object plane, either coherent or noncoherent light can be used to illuminate the fluid. If the position of the particles is not known or controlled, imaging system 20 can form an image of fluid 200 using a plane at any position across fluid chamber 55 for the object plane. Preferably, the object plane will be at or near the center of fluid chamber 55 so that the maximum distance from the object plane that particles may be located can be minimized. The distance is minimized because, the closer a particle is to the object plane, the better the resolution of the particle in the image. When the position of the particles is not known or controlled, a coherent light source is preferred. Coherent light is preferred because it increases the distance from the object plane that particles can be located and yet maintain their shape in an image of the fluid. The shape of the particle can be maintained in an image if coherent light is used and the diffraction pattern is characteristic of the optical near field. Therefore, the shape of a particle at any position across the fluid chamber will be maintained in the image of the fluid chamber if the fluid chamber is illuminated with coherent light and the diffraction pattern of the light exiting the fluid chamber is characteristic of the optical near field.

Imaging system 20 can form either a direct image of the fluid volume or its optical Fourier transform depending upon the requirements of the image processor 60. The imaging can be accomplished by any of several conventional means including, but not limited to, lenses, mirrors, or coherent optical fiber bundles (proximity focusing). If space is limited, imaging system 20 may use mirrors (not shown) to route beam 18 to gain the proper distance needed to focus the image of fluid chamber 55 onto optical detector 72.

The dimensions of fluid chamber 55 can be any size. However, as discussed above, it is preferable that width of fluid chamber 55 be such that the diffraction pattern of the light exiting the fluid chamber is characteristic of the optical near field. Additionally, in selecting length of fluid chamber 55, and the width (in the direction orthogonal to the sheet in FIG. 1) of fluid chamber 55 consideration should be given to the expected size of the particles and the size of the image created.

Figure 4A:
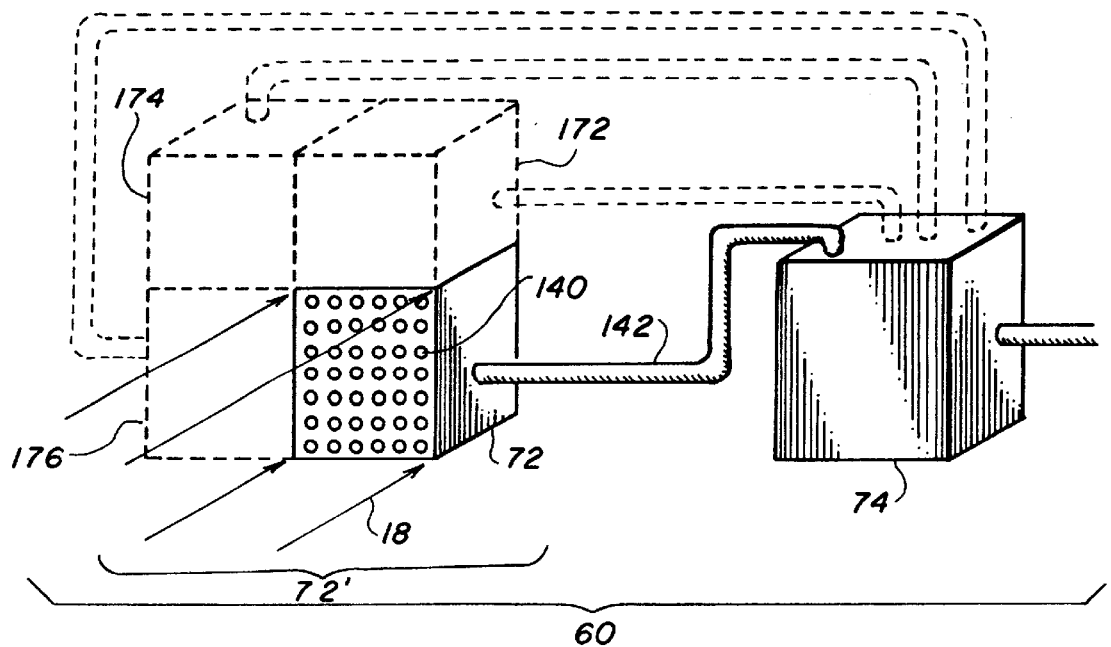
FIGS. 4A and 4B show two embodiments of a detection and image processor.

FIG. 4A shows a preferred embodiment of image processor 60. Optical beam 18 from the imaging system (not shown) carries the image of the fluid within the fluid chamber to optical detector 72. Optical detector 72 has an optically sensitive surface containing a two dimensional planar array of opto-electric converters 140 each of which constitutes an image pixel. Output 142 of detector 72 is connected to shape classifier 74 which analyzes the output of detector 72 and identifies the size and shape of a particle in two dimensions based on characteristic patterns (straight lines, corners, curves, etc.).

In operation, optical detector 72 is illuminated by beam 18 for each pulse by the source (as described above in reference to FIG. 1). Upon illumination of optical detector 72 by beam 18, each opto-electric converter 140 creates electronic data proportional to the intensity of light from beam 18 received at the converter. Because the electronic data produced at each converter 140 is proportional to the intensity of the light received, variations in the intensity of the image are maintained in the electronic data. Thus, the optical image formed on the face of detector 72 is converted into electronic data that is capable of subsequent electronic reading and processing.

Because only the portion of the image which is formed on optical detector 72 will be converted into electrical signals, the dimensions of the image produced and the dimensions of detector 72 should correspond to each other. Additionally, to determine the size of a particle within the desired degree of spatial resolution, the distance between the centers of each image pixel (converter) 140 on optical detector 72 should be no larger than the unit of resolution. For instance, if the desired degree of spatial resolution is 10 $\mu$m, the distance between the centers of any two horizontally or vertically adjacent pixels 140 should be less than or equal to 10-$\mu$m.

Also, several optical detectors can be combined in an array to form a larger optical detector. This arrangement is represented in FIG. 4A by the combination of optical detectors 172, 174, and 176 along with optical detector 72 to form optical detector array 72'. The output of each individual detector (72, 172, 174, 176) in the array will be connected to shape classifier 74. Additionally, when several detectors are combined into this type of array, the image pixels located next to the edge of the detector should be sufficiently close to the edge of the detector such that the distance between the centers of two horizontally or vertically adjacent pixels on neighboring detectors is less than or equal to the desired spatial resolution.

Converter 140 in detector 72 can have an associated charge coupled device (CCD) element which receives a charge proportional to the intensity of light at the converter. The CCD element can be read to provide an output value corresponding to the charge received at the element. The CCD elements can be read serially providing at output 142 a single string of output values or the CCD's can be read in parallel such that all the CCD elements are read simultaneously providing a plurality of output 142 connections with each individual output 142 containing a single output value from a single CCD. Similarly, converter 140 in detector 72 can be a phototransistor. The phototransistor will produce a response, such as a current gain, proportional to the amount of light received. The size of the response produced by the phototransistor can be used to provide an output value corresponding to the intensity of light received at the phototransistor. Similarly, the output 142 from detector 72 comprised of phototransistors can be read serially or in parallel.

Figure 4B:
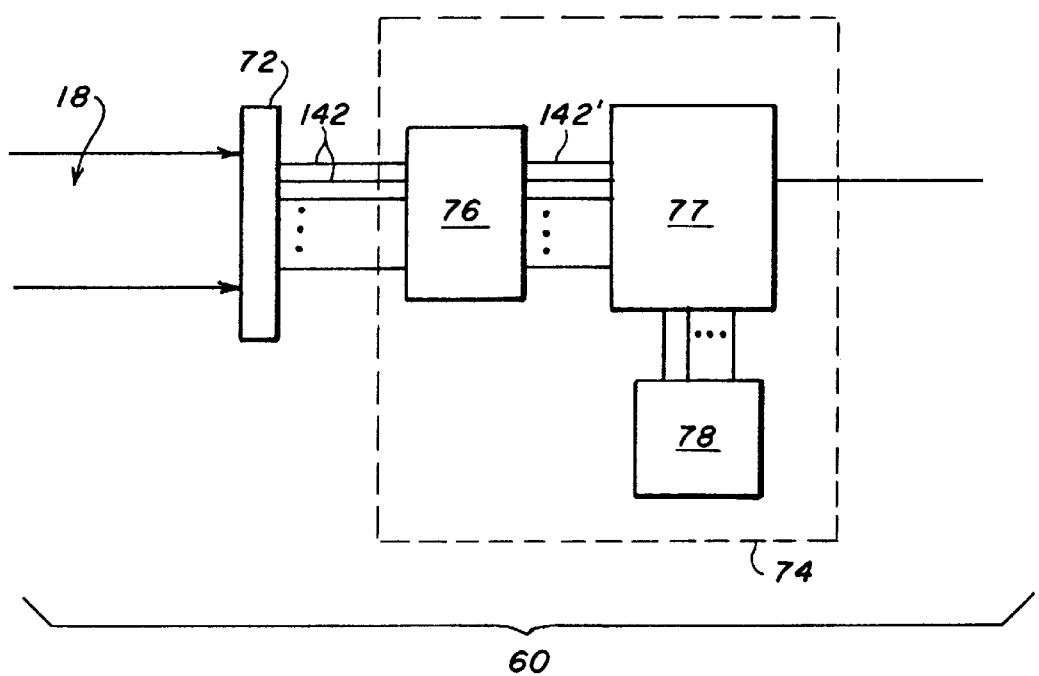

The output data from detector 72 is sent to shape classifier 74. Shape classifier 74 can process the output data from detector 72 using an appropriate pattern recognition or pattern matching technique, such as van der Lugt correlation or Bayesian classification, to determine the size and shape of particles in the fluid. The exact operation of shape classifier 74 will depend upon the type of pattern recognition or pattern matching algorithm chosen of which many types are currently known. FIG. 4B shows an illustration of the embodiment of shape classifier 74.

In FIG. 4B, shape classifier 74 performs a correlation algorithm, the shape classifier will typically contain a microprocessor 77 which will use the output data from detector 72 along with information stored in memory means 78 to perform the correlation function. Optionally, the shape classifier can contain a preprocessor 76 the operation of which will be discussed below.

In operation, the image of the fluid is formed on the face of detector 72. The detector converts the optical image into electronic data as previously explained. The output data from detector 72 is sent to shape classifier 74. Preferably, the data is output in parallel, as shown in FIG. 4B, over multiple output connections 142. Thus, electronic data representing an input image from detector 72 is received by shape classifier 74. Using the data for the input image obtained from detector 72 and data for reference images stored in memory means 78, microprocessor 77 can perform a correlation algorithm, such as van der Lugt correlation.

Image correlation is based on the correlation theorem:

$$A_I(x,y) \otimes A_R(x,y) = F^{-1}[F(A_I(x,y))F^*(A_R(x,y))]$$

where $A_I$ and $A_R$ represent the input and reference images, $\otimes$ denotes the operation of correlation, F denotes the Fourier transform, and * denotes the complex conjugate. Mathematical correlation of two images will produce a correlation value corresponding to the degree of similarity of the two images. Images of particles of roughly the same size and shape will result a high correlation product. By performing a correlation of the input image with the reference images and determining which correlation product has the largest value, the size and shape of the particle can be determined.

To improve the performance of microprocessor 77, preprocessor 76 can be used. The preprocessor can be used to perform an intermediate transform, such as a Hough transform, to remove rotational and size dependence. By removing these dependencies, the number of reference images can be reduced thereby reducing the number of correlation products which must be produced. Additionally, preprocessor 76 can implement traditional image processing techniques to segment and find areas of the image where particles are represented and to delineate the boundary of such objects. By only passing the data from the input image which contains the image of a particle, the amount of data which is sent to microprocessor 77 for correlation is reduced. Similarly, preprocessor 76 can be used to identify certain types or classes of particles which do not need to be identified by size and shape. For example, for the application of monitoring particles in the oil of aircraft engines, it is expected that the debris in the oil will be nonspherical. Therefore, it can be assumed that all round particles are entrained air bubbles. By using traditional image processing techniques, such as calculating the curvature around an image, data corresponding to round particles does not need to be processed by microprocessor 77. This will reduce the computational requirements of microprocessor 77 in systems where the number of bubbles greatly exceeds the number of particulates.

Figure 2:
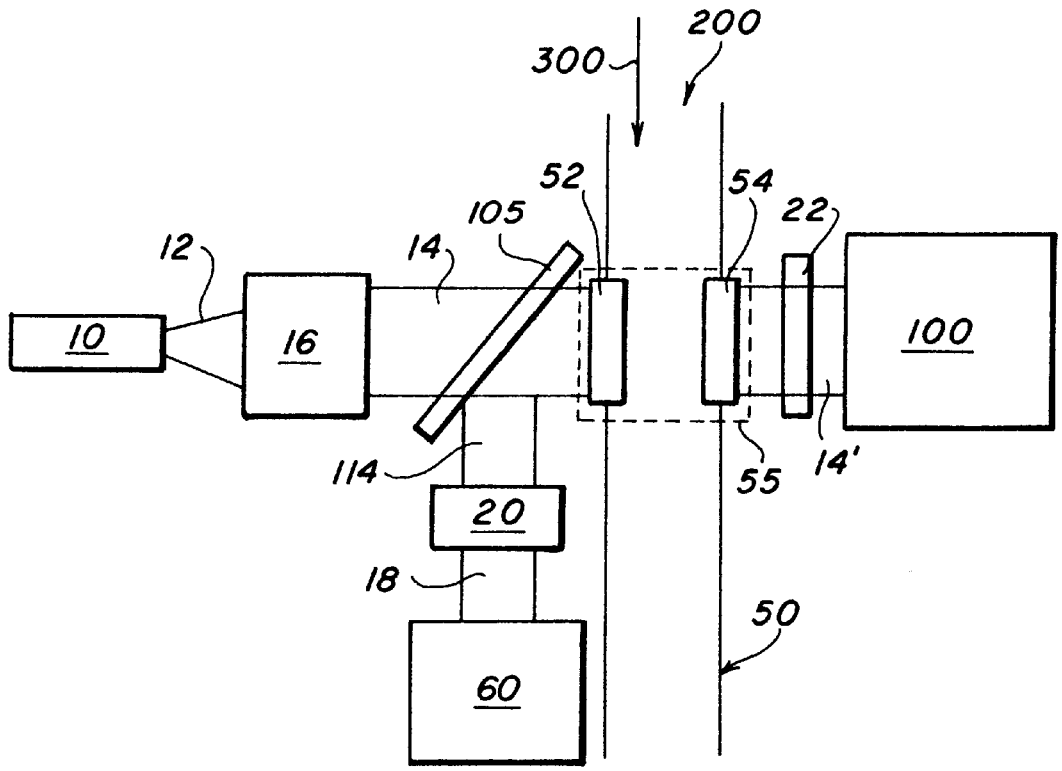
FIG. 2 is a schematic diagram showing a second embodiment.

A second embodiment of the present invention is shown in FIG. 2. In the embodiment of FIG. 2, the characteristics, requirements, and operation of elements with reference numerals identical to those in FIG. 1 are the same as previously described in reference to FIG. 1.

In FIG. 2, source 10 provides an optical beam 12 to the collimating optics 16 which produces a collimated beam 14 which is directed toward beam splitter 105. Beam splitter 105 allows a portion of beam 14 to pass through and continue on in the direction toward fluid chamber 55 while reflecting a portion of beam 14 in a direction away from imaging system 20. The portion of beam 14 directed away from imaging system 20, is lost from the system. Collimated beam 14 which has passed through beam splitter 105 enters the fluid chamber 55 through window 52, propagates through fluid 200, and exits through window 54. After exiting fluid chamber 55, optical system 22 focuses transmitted beam 14' into phase conjugate reflector 100.

Phase conjugate reflector 100 precisely changes the direction of propagation of the incident beam in such a way that the return beam retraces the same path as the incident beam. The return beam travels back through imaging system 22, entering fluid chamber 55 through window 54 and exiting through window 52. The return beam is then split by beam splitter 105 which directs a portion of the return beam toward imaging system 20 while allowing the remaining portion to pass through and continue in the same direction of propagation. Imaging system 20 forms either a direct image of the center of the fluid chamber or its optical Fourier transform, onto optical detector 72 of image processor 60.

As in the previous embodiment, light source 10 is pulsed so a "stop action" image of fluid 200 flowing through fluid chamber 55 is created at detector 72. Collimated beam 14' transmitted through the chamber is focused onto phase conjugate reflector 100 by optical system 22. Optical system 22, which can be a lens, is used to capture beam 14' exiting fluid chamber 55 and focus beam 14' onto phase conjugate reflector 100. Optical system 22 is placed an arbitrary distance from window 54 or the imaging system can be incorporated into window 54. Phase conjugate reflector 100 precisely changes the direction of propagation of the incident beam causing the return beam to follow the same path through imaging system 22 and fluid chamber 55 as the incident beam. After exiting fluid chamber 55, the return beam is directed to imaging system 20 which forms an image of an object plane within fluid 200 onto optical detector 22 in image processor 60. This image is then analyzed by image processor 60. Once again, a new image of fluid 200 within fluid chamber 55 will be created each time source 10 is pulsed, and therefore, the analysis should be completed in the time between pulses, or in the time between indications by preprocessor 76 that non spherical particulates occur in fluid 200. The operation of image processor 60 is as described above in reference to FIGS. 4A and 4B.

Figure 5A:
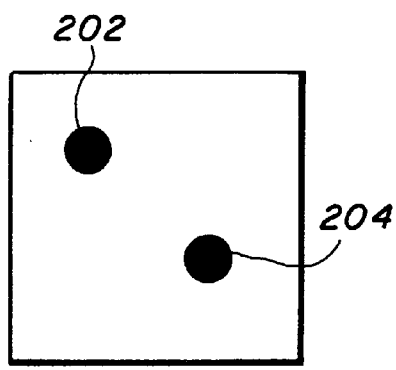
FIGS. 5A and 5B show examples of images of the center of a fluid chamber.

FIG. 5A shows an example of an image formed at the optical detector of the device described in reference to FIG. 1. The image in FIG. 5A shows how an air bubble 202 and a nearly spherical particle 204 appear on the face of the optical detector. Air bubble 202 in the fluid appears in the image as a dark circle against a bright background due to the scattering of the light by the air bubble. Suspended particle 204 also appears as a dark shadow against a bright background because the light is absorbed by the particle.

Figure 5B:
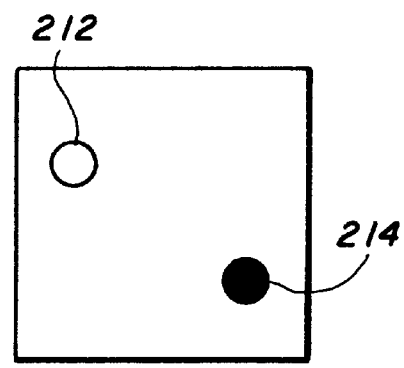

FIG. 5B, on the other hand, shows how the same image would appear on the optical detector of the embodiment described in FIG. 2. As can be seen in FIG. 5B, air bubble 212 appears as a dark ring against a light background while the image of the suspended particle 214 remains a dark shadow. Thus, in an application where one expects to see spherical or very nearly spherical particles in the fluid, the embodiment of FIG. 2, allows the application to distinguish air bubbles from spherical particles.

Figure 3:
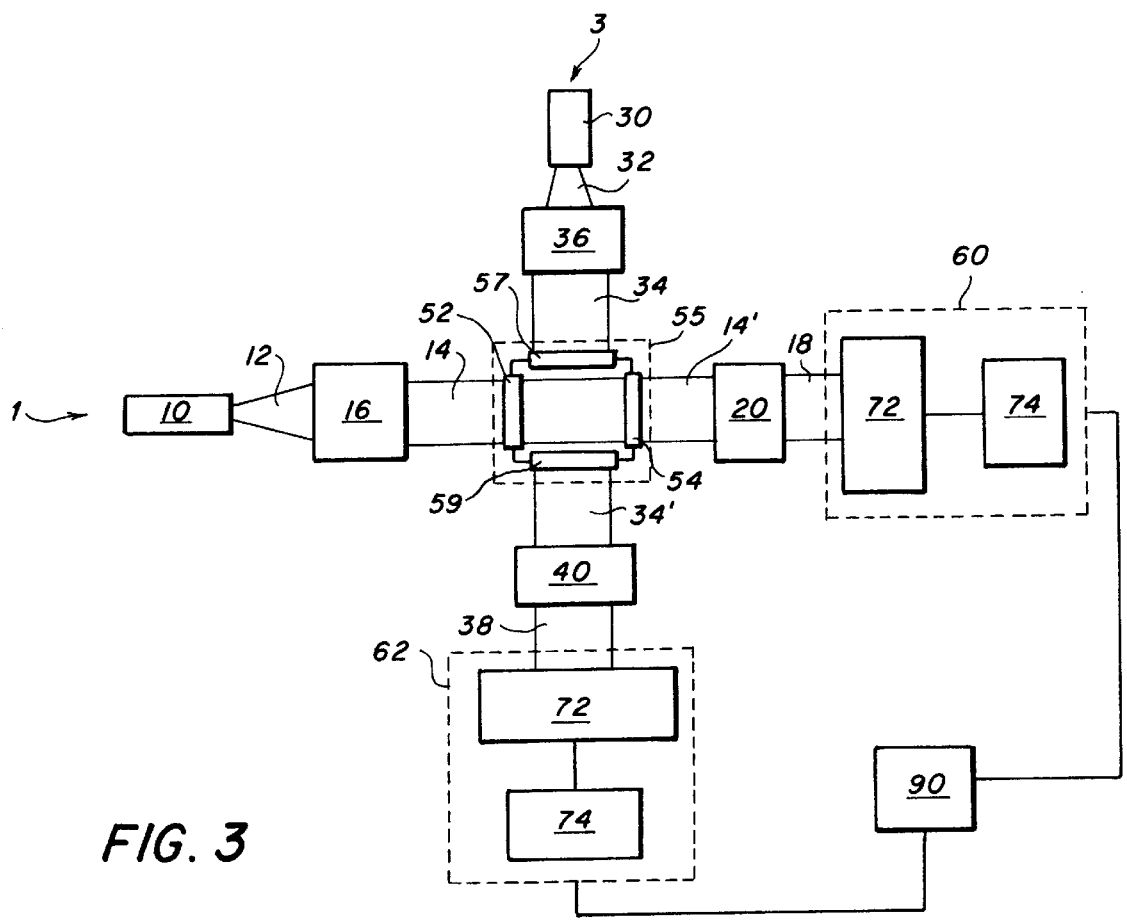
FIG. 3 is a schematic diagram showing a third embodiment.

A third embodiment of the present invention, shown in FIG. 3, incorporates two of the devices described in reference to FIG. 1 around a single fluid chamber 55. Preferably, the devices 1 and 3 are combined in such a way that the two collimated beams 14 and 34 entering the fluid chamber are essentially orthogonal to each other, as well as to fluid chamber 55. In this embodiment shown in FIG. 3, the direction of the flow of the fluid (not shown) through the fluid chamber 55 can be either into or out of the sheet.

Sources 10 and 30 provide optical beams 12 and 32, respectively. The two optical beams 12 and 32 are collimated by collimating means 16 and 36, respectively. A first collimated beam 14 enters fluid chamber 55 through window 52, propagates through the fluid, and exits fluid chamber 55 through window 54. Imaging system 20 acts on collimated beam 14' that has passed through fluid chamber 55 to form an image with an object plane within fluid chamber 55 onto optical detector 72 of image processor 60. Simultaneously, a second collimated beam 34 enters the fluid chamber 55 through window 57, propagates through the fluid, and exits through window 59. Imaging system 40 acts on collimated beam 34' exiting fluid chamber 55 to form an image the fluid within fluid chamber 55 onto optical detector 72 of image processor 62.

The outputs of the image processors 60 and 62, containing information on the size, shape, and position of the particles in two dimensions, are combined together in shape processor 90 to obtain size and shape information for three dimensions. Shape processor 90 can be used to calculate simple information such as volume of the particle or it can be used to calculate more complex information for three dimensions to further classify particle types such as flakes, crystallites or cubes.

In this embodiment, the characteristics, operation, and requirements of sources 10 and 30, collimating optics 16 and 36, fluid chamber 55, windows 52, 54, 57, and 59, and imaging systems 20 and 40 are as previously described in reference to FIG. 1.

In operation, sources 10 and 30 are pulsed simultaneously with the pulse duration and pulse repetition rate chosen with regard to the flow speed of the fluid. The duration of the pulse should be short enough so that during the pulse the particles do not move by more than the desired spatial resolution. The repetition rate is set so that, in the time between pulses, the fluid travels a distance equal to the length, in the direction of fluid flow, of the fluid imaged. The wavelength of each source must be such that the light can be transmitted through the fluid in sufficient quantity to be detectable yet at the same time be absorbed by the particulate matter within the fluid. However, the wavelengths of the sources need not be identical.

The operation of image processors 60 and 62 is as described above in reference to FIG. 4A. Additionally, data from image processors 60 and 62, containing information on the size, shape, and position of the particles in two dimensions, should be combined together in a shape processor 90 to obtain size and shape information for three dimensions.

While the embodiment of the present invention shown in FIG. 3 combines two of the devices in FIG. 1 around a single fluid chamber 55, it is also possible to combine three or more of the devices shown in FIG. 1 around a single fluid chamber to obtain more detailed information. Additionally, another variation can be had by combining two or more of the devices of FIG. 2 around a single fluid chamber.

What is claimed is:

1. An apparatus for the real time monitoring of suspended particulates in a fluid, said apparatus comprising:
   a laser light source;
   means for collimating an optical beam from said light source;
   a fluid chamber for passing a fluid to be examined, said fluid chamber being suitable for illumination by said collimated beam;
   means for forming an optical image of the fluid within said fluid chamber; and
   means for classifying shapes of particulates in said optical image;
   wherein said means for classifying shapes comprises:
      a two-dimensional transducer array means for detecting said optical image and
      means for comparing, responsive to said means for detecting, shapes of the particulates in the fluid with at least one reference shape.

2. The apparatus of claim 1 wherein:
   said light source emits coherent light;
   said means for forming an optical image comprises a lens; and
   said means for detecting said optical image comprises an array of phototransisters.

3. The apparatus of claim 1 wherein:
   said light source emits coherent light; and
   said means for detecting said optical image comprises an array of phototransisters.

4. The apparatus of claim 1 wherein:
   said light source emits coherent light;
   said means for forming an optical image comprises a lens; and
   said means for detecting said optical image comprises an array of charge coupled devices.

5. The apparatus of claim 1 further comprising:
   a second light source;
   a second means for collimating an optical beam from said light source;
   a second means for forming an optical image of the fluid within said fluid chamber; and
   a second-means for classifying shapes of particulates in said optical image.

6. The apparatus of claim 5 wherein:
   said means for classifying shapes of particulates comprises a first means for detecting said optical image and a first means for comparing, responsive to said first means for detecting, shapes of the particulates in the fluid with reference shapes and
   said second means for classifying shapes of particulates comprises a second means for detecting said optical image and a second means for comparing, responsive to said second means for detecting, shapes of the particulates in the fluid with reference shapes.

7. The apparatus of claim 6 wherein:
   said first means for classifying shapes of particulates comprises a first memory means for storing information relating to reference shapes and a first means for processing said information relating to reference shapes with information from said first means for detecting said optical image to classify the shapes of particulates within said fluid captured in said optical image and
   said second means for classifying shapes of particles comprises a second memory means for storing information relating to reference shapes and a second means for processing said information relating to reference shapes with information from said second means for detecting said optical image to classify the shapes of particulates within said fluid captured in said optical image.

8. The apparatus of claim 1, wherein said means for comparing comprises:
   means for storing in computer memory a reference shape indicative of a particulate shape having a circular cross-section;

electronic means for comparing said reference shape to said optical image effective to identify particulates whose shape matches said reference shape.

9. The apparatus of claim 1, wherein said apparatus comprises Hough transform means for removing rotational and size dependance of said particulates in said optical image.

10. The apparatus of claim 1, wherein said means for comparing comprises a means for spatially correlating said image and said reference shape.

11. The apparatus of claim 1, wherein said electronic means is a neural net adapted to compare said reference shape to said image.

12. The apparatus of claim 1, wherein said means for comparing comprises:

means for forming a transformed image by performing a spatial Fourier transform on said image;

means for comparing a preselected spatial Fourier spectrum to said transformed image.

13. The apparatus of claim 1, wherein said light source is a pulsed light source.

14. A method for the real time monitoring of suspended particulate matter in a fluid, said method comprising the steps of:

a) illuminating a fluid with a laser beam;

b) forming an optical image of the illuminated fluid;

c) detecting said optical image of the fluid with a two-dimensional transducer array; and d) analyzing said optical image of the fluid wherein said analyzing comprises:

retrieving from computer memory at least one particulate matter reference shape;

electronically comparing said image to said at least one particulate matter reference shape to match said at least one reference shape to shapes present in said image.

15. The method of claim 14 wherein:

the fluid is illuminated by a, collimated optical beam and the optical image is analyzed by a microprocessor.

16. The method of claim 14 wherein:

the fluid is illuminated by a, collimated optical beam and the optical image is analyzed by an optical correlator.

17. The method of claim 14 wherein:

the fluid is,illuminated by a, collimated optical beam and the optical image is analyzed by a neural network.

18. The method of claim 14, wherein said method comprises applying a Hough transform to said image effective to remove rotational and size dependance of said particulate matter in said image.

19. The method of claim 14, wherein said analyzing comprises spatially correlating said image and said particulate matter reference shape.

20. The method of claim 14 wherein said electronically comparing comprises using a neural net to compare said particulate matter reference shape to said image.

21. The method of claim 14, wherein said electronically comparing comprises spatial correlating said image and said at least one particulate matter reference shape.

22. The method of claim 14, wherein said electronically comparing comprises:

forming a Fourier transform of said image;

comparing a preselected spatial Fourier spectrum to said Fourier transform of said image.

23. The method of claim 14 wherein said illuminating employs pulsed illumination.

24. An apparatus for the real time monitoring of suspended particulates in a fluid, said apparatus comprising:

a laser light source;

means for collimating an optical beam from said light source;

a fluid chamber for passing a fluid to be examined, said fluid chamber being suitable for illumination by said collimated optical beam;

means for optical phase conjugation of said collimated beam on the side of said fluid chamber opposite to that which said light enters said chamber;

a first imaging means, arranged between said fluid chamber and said means for optical phase conjugation for focusing said collimated beam exiting said fluid chamber onto said phase conjugation means;

a second imaging means for forming an optical image of the fluid within said fluid chamber by capturing said collimated beam after said collimated beam has propagated from said optical phase conjugation means through said fluid chamber; and wherein each of said first and said second imaging means is a two-dimensional opto-electric array; and wherein said apparatus further comprises means for processing said optical image.

25. The apparatus of claim 24 wherein:

said light source emits coherent light;

said means for forming an optical image comprises a lens; and said means for detecting said optical image comprises an array of phototransisters.

26. The apparatus of claim 24 wherein:

said light source emits coherent light; and said means for detecting said optical image comprises an array of phototransisters.

27. The apparatus of claim 24 wherein:

said light source edits coherent light;

said means for forming an optical image comprises a lens; and said means for detecting said optical image comprises an array of charge coupled devices.

28. The apparatus of claim 24, wherein said means for processing comprises:

electronic means for comparing said reference shape to said optical image effective to identify particulate whose shape matches said reference shape.

29. The apparatus of claim 28 wherein said apparatus comprises Hough transform means for removing rotational and size dependance of said particulate in said optical image.

30. The apparatus of claim 28, wherein said electronic means comprises means for spatially correlating said image and said reference shape.

31. The apparatus of claim 28 wherein said electronic means is a neural net adapted to compare said reference shape to said image.

32. The apparatus of claim 28, wherein said electronic means comprises a spatial correlator for correlating said image and said at least one reference shape.

33. The apparatus of claim 24, wherein said means for processing comprises:

means for forming a transformed image by performing a spatial Fourier transform on said image;

means for comparing a preselected spatial Fourier spectrum to said transformed image.

34. The apparatus of claim 24 wherein said light source is a pulsed light source.

* * * * *